United States Patent
Bornscheuer et al.

(10) Patent No.: US 8,017,354 B2
(45) Date of Patent: Sep. 13, 2011

(54) MICROORGANISM FOR PRODUCING RECOMBINANT PIG LIVER ESTERASE

(75) Inventors: Uwe Bornscheuer, Greifswald (DE); Dominique Boettcher, Sponholz (DE); Elke Bruesehaber, Greifswald (DE); Kai Doderer, Rodgau (DE)

(73) Assignee: Enzymicals AG, Greifswald (DE)

( * ) Notice: Subject to any disclaimer, the term of this patent is extended or adjusted under 35 U.S.C. 154(b) by 111 days.

(21) Appl. No.: 12/504,785

(22) Filed: Jul. 17, 2009

(65) Prior Publication Data

US 2010/0021964 A1    Jan. 28, 2010

Related U.S. Application Data

(60) Provisional application No. 61/082,039, filed on Jul. 18, 2008.

(51) Int. Cl.
*C12P 1/00* (2006.01)
*C12N 1/00* (2006.01)
*C12N 1/20* (2006.01)

(52) U.S. Cl. .................... 435/41; 435/243; 435/252.3

(58) Field of Classification Search .................... None
See application file for complete search history.

(56) References Cited

OTHER PUBLICATIONS

Hummel et al. (Isoenzymes of Pig-Liver Esterase Reveal Striking Differences in Enantioselectivities, Angew. Chem. Int. Ed. 2007, 46, 8492-8494).*
Matsushima et al. (The nucleotide and deduced amino acid sequences of porcine liver proline-_-naphthylamidase, FEBS Letters, vol. 293, No. 1.2, pp. 37-41, 1991).*
Anke Hummel, et al., "Isoenzymes of Pig-Liver Esterase Reveal Striking Differences in Enantioselectivities", Angew. Chem. Int. Ed. 2007, 46, pp. 8492-8494.

* cited by examiner

*Primary Examiner* — Suzanne Noakes
*Assistant Examiner* — Jae W Lee
(74) *Attorney, Agent, or Firm* — Oblon, Spivak, McClelland, Maier & Neustadt, L.L.P.

(57) ABSTRACT

The present invention relates to a microorganism which comprises at least one copy of a polynucleic acid sequence which is foreign to the host and which encodes a protein having an enzymic activity, and comprises a chaperone system which assists the expression of the protein in the form of an active enzyme, and to a method for producing a protein having esterase activity using such a microorganism.

11 Claims, 1 Drawing Sheet

MICROORGANISM FOR PRODUCING RECOMBINANT PIG LIVER ESTERASE

This application incorporates by reference the disclosure of DE 10 2006 031600.2, filed Jul. 6, 2006 in its entirety. Polynucleotide and amino acid sequences are specifically incorporated by reference to the documents disclosing them or to the commercial sources mentioned in the following disclosure.

The present invention relates to a microorganism which comprises at least one copy of a polynucleic acid sequence which is foreign to the host and which encodes a protein having an enzymic activity, and comprises a chaperone system which assists the expression of the protein in the form of an active enzyme, and to a method for producing a protein having esterase activity using such a microorganism.

Lipases and esterases are suitable as efficient biocatalysts for the preparation of a large number of optically active compounds. Whereas, however, a whole series of lipases—especially of microbial origin—are commercially available, only very few esterases are available for use in a racemate resolution in industrial quantities [Bornscheuer, U. T. and Kazlauskas R. J., Hydrolases in Organic Synthesis (2005), $2^{nd}$ ed, Wiley-VCH, Weinheim].

In this connection there is particular interest in pig liver esterase because of its interesting catalytic properties in organic synthesis [Faber, K., Biotransformations in Organic Chemistry (2004), $5^{th}$ ed. Springer, Berlin; Jones, J. B. Pure Appl. Chem, (1990), 62, 1445-1448, Jones et. al. Can. J. Chem. (1985), 63, 452-456; Lam, L. K. P. et. al., J. Org. Chem. (1986), 51, 2047-2050].

Although it has been possible to show that stereoselective conversion of substrates is possible in some cases with esterase extracts from pig liver tissue, the use of such extracts is associated with a number of disadvantages, however. Besides variations in the esterase content between different batches, the presence of other hydrolases is to be regarded in particular as problematic in relation to stereoselectivities (Seebach, D. et. al, 25 Chimia (1986), 40, 315-318). There is in addition the problem that the conventional extracts take the form of a plurality of isoenzymes (Farb, D., et. al, Arch. Biochem. Biophys. (1980) 203, 214-226) which in some cases differ considerably in their substrate specificity. Heymann, E. and Junge, W. (Eur. J. Biochem. (1979), 95, 509-518; Eur. J. Biochem. (1979), 95, 519-525) achieved an elaborate electrophoretic separation making it possible to isolate fractions which preferentially cleave butyrylcholine, proline β-naphthylamide and methyl butyrate. In contrast thereto, other investigations (e.g. Lam, L. K. P., et. al, J. Am. Chem. Soc. (1988) 110, 4409-4411) merely show differences in the activity, but not in the specificity of individual fractions.

For this reason, there is a need for biotechnologically produced pig liver esterases with a defined composition.

Although cloning of putative pig liver esterase genes has been known for some time (Takahashi, T, et. al., J. Biol. Chem. (1989), 264, 11565-11571; FEBS Lett. (1991), 280, 297-300; FEBS Lett. (1991), 293, 37-41; David, L. et. al, Eur. J. Biochem. (1998) 257, 142-148), the functional, recombinant expression of an active pig liver esterase has been achieved to date, despite considerable efforts owing to the existing demand for this enzyme, only in *Pichia pastoris* (Lange, S. et al., ChemBioChem (2001), 2, 576-582). The productivities achieved in this case are very low, at 0.5 U/ml of culture supernatant after fermentation for 96 hours, and are thus unsatisfactory for commercial production of the pig liver esterase. It would additionally be desirable to use *Escherichia coli* as expression system, because this expression system is associated with the advantages mentioned below.

Systems based on *Escherichia coli* for heterologous expression have many advantages over other expression hosts (Makrides, S C, Microbiol Rev (1996), 60, 512-582) for producing large quantities of recombinant proteins. The principal advantages are the rapid growth of *Escherichia coli* cells, the high content of heterologously expressed protein and the detailed knowledge of the biology, the metabolism and the genetics of these organisms. It is nevertheless not possible for every gene to be produced heterologously, actively and with good productivities in *Escherichia coli*. This may be due to the unique and unpredictable properties of the gene, the stability and the translational efficiency of the messenger RNA (mRNA), the degradation of the recombinant protein by proteases intrinsic to the cell or fundamental differences in the codon usage of the expression host and of the foreign gene (Jana, S. et al., Appl. Microbiol. Biotechnol. (2005), 67, 289-298).

Expression in bacterial hosts may in addition generally have some fundamental disadvantages, especially if the heterologously expressed protein(s) is/are derived from eukaryotic sources. In many cases, the recombinant protein is then inappropriately folded and thus insoluble and inactive. The reasons for this are based on the fact that, owing to the biology of *Escherichia coli*, no post-translational modifications corresponding to the eukaryotic systems are carried out, such as, for example, glycosylations and others (e.g. Jana, S. et al., Appl. Microbiol. Biotechnol. (2005), 67, 289-298 and all references therein). It is likewise impossible for the recombinant target protein to be secreted into the medium. This is necessary for the functional folding of many proteins (e.g. Jana, S. et al., Appl. Microbiol. Biotechnol. (2005), 67, 289-298 and all references therein). The ability of *E. coli* cells to form disulphide bridges in the target protein is likewise very limited. Since efficient and correct formation of disulphide bridges is, however, essential for functional folding of many proteins, this is a very important point.

Investigations of esterase extracts from pig liver show that the individual isoforms of the proteins are glycosylated. This likewise applies to the isoform produced recombinantly in *Pichia pastoris* (Lange, S. et. al., ChemBioChem (2001), 2, 576-582).

*E. coli* expression systems described in the literature for the heterologous expression of proteins have been tested by comparison with the present invention. The attempt to express pig liver esterase in *Escherichia coli* BL21 Star™ (DE3) led to overexpression of the protein in the form of inclusion bodies. However, no pig liver esterase activity was detectable in the *E. coli* crude cell extract, although the *E. coli* strain BL21 Star™ (DE3) used lacks two important proteases which are responsible for the degradation of expressed proteins (see comparative example 1). The lack of such proteases usually means a marked reduction in the degradation of the heterologously expressed proteins.

*E. coli* Rosetta (DE3) was used as further *E. coli* expression strain. Six tRNAs for codons which are represented very rarely in wild-type *E. coli* strains have been added to this expression host. This usually leads to improvement in the expression of foreign proteins, especially of eukaryotic origin [Novy, R. et. al., inNovations (2001), 12, 1-3]. Use of this expression strain also led only to expression in the form of inclusion bodies. No pig liver esterase activity was detectable in the supernatant after cell disruption (see comparative example 2).

The formation of disulphide bridges in a heterologously expressed target protein can be improved through the use of an *E. coli* strain which has mutations in the thioredoxin reductase gene and glutathione reductase gene and thus improves the conditions for the formation of disulphide bridges in the cytosol of *E. coli* [Besette, P. H. et. al., Proc. Natl. Acad. Sci. USA (1999), 96, 13703-13708)]. *E. coli* Origami (DE3) has this modification and was used for the expression of the pig liver esterase. The expression detected in this case took place exclusively in the form of inclusion bodies, and no pig liver esterase activity was detectable in the crude cell extract (see comparative example 3).

It is possible in many cases to achieve functional expression by reducing the inducer concentration (Thomas, J G, Protein Expression and Purif. (1997), 11, 289-296). This was carried out using the *E. coli* Rosetta-gami (DE3) strain. This strain combines all the properties of the three *E. coli* strains described above, and the level of expression of a protein can be adapted by varying the inducer concentration (use of IPTG as inducer). Even with this procedure and by reducing the IPTG concentration, most of the expression of the heterologous protein took place in the form of inclusion bodies and, after disruption of the *E. coli* cells, only a low, commercially unattractive pig liver esterase activity was detectable (see comparative example 4).

The literature likewise describes additions to the medium during expression in *E. coli*. Addition of up to 3% (v/v) ethanol to the medium induces the formation of chaperones belonging to *E. coli*, enzymes which serve as folding aids and usually assist correct folding (Thomas, J G, Protein Expression and Purif (1997), 11, 289-296). Expression of pig liver esterase in *E. coli* Origami (DE3) with addition of 3% (v/v) ethanol to the medium likewise led to no detectable active expression of the esterase in *E. coli* (see comparative example 5), but only to inclusion bodies.

It can be stated in summary that to date no functional expression of pig liver esterase in *Escherichia coli* has yet been reported. However, in order to utilize the advantages described above for the *Escherichia coli* expression system, it was an object of the present invention to find a system and a method for the functional expression of a desired heterologous enzyme in an *Escherichia coli* host.

The object is achieved by a microorganism comprising at least one copy of a polynucleic acid sequence which is foreign to the host (heterologous) and which encodes a protein having an enzymic activity, and a chaperone system which assists the functional expression of the protein in the form of an active enzyme, and a method for producing a functional enzyme using such a microorganism.

A host organism according to the invention which is preferred and particularly suitable is an *E. coli* strain whose expression properties are known. It is particularly preferred for the *E. coli* strain to be able to carry out certain post-translational modifications on the expressed protein, e.g. the formation of disulphide bridges or, where appropriate, also glycosylations. It is likewise preferred for the strain to provide a possibility for regulating expression and/or for proteins belonging to the host and reducing the expression yield (e.g. proteases) to be deleted.

A preferred enzyme which can be expressed with the aid of such a microorganism is an esterase, preferably an esterase from mammals, particularly preferably a porcine esterase which is naturally expressed in the pig liver. Such an esterase preferably has a stereoselective catalytic activity. A particularly preferred esterase is one encoded by the cDNA sequence SEQ ID No. 1 or fragments thereof, or by a sequence which is homologous to this sequence or fragments thereof. It may be sufficient for the present invention if fragments of SEQ ID NO. 1 or of a sequence homologous thereto are expressed and lead to amino acid sequences which possess a catalytic activity which corresponds to the desired activity. A preferred esterase thus has an amino acid sequence SEQ ID No. 5 or a homologous sequence, or fragments thereof which possess a catalytic activity.

A homologous sequence in connection with the present invention means, at the polynucleic acid level (i.e. at the DNA/RNA level), a sequence which, owing to the degeneracy of the genetic code, leads to the same amino acid sequence which is also encoded by SEQ ID No. 1 (this corresponds to 100% homology), in particular a sequence which is adapted for example to the species-specific codon usage of the host, or a polynucleic acid sequence which encodes a homologous protein, it being necessary in this case also to take account of the degeneracy of the genetic code. A sequence is homologous at the protein level (a homologous protein) according to the present invention if the amino acid sequence of the protein has been modified by comparison with SEQ ID No. 5 in such a way that a catalytic esterase activity still exists. The amino acid sequence is preferably modified by comparison with SEQ ID No. 5 in such a way that at least 70%, preferably at least 80%, further preferably at least 90% and particularly preferably at least 95% of the amino acids are identical to the respective amino acids in the same position in the sequential arrangement. It is additionally preferred for the amino acids which have been modified by comparison with SEQ ID No. 5 to be "homologous amino acids", i.e. in each case an amino acid which resembles the amino acid present at the corresponding position in SEQ ID No. 5 in charge, steric extent and polarity. Examples of a homologous amino acid exchange are the exchange of alanine, serine or threonine for one another, aspartate and glutamate for one another, asparagine and glutamine for one another, arginine and lysine for one another, isoleucine, leucine, methionine and valine for one another, and phenylalanine, tyrosine and tryptophan for one another, without obligatory restriction thereto.

Enzymes which are likewise to be regarded as homologues of the enzyme described herein are those which have in their catalytic region a homology which complies with the above definition, but differ in the N-terminal or C-terminal region from SEQ ID No. 5. Possible examples thereof are in particular splice variants of the present enzyme which, however, have the same or a very similar activity as the enzyme with SEQ ID No. 5, or else tissue-specific variants of the enzyme.

The sequence which codes for the desired protein to be expressed is preferably introduced with the aid of a plasmid into the host cell. For this purpose, the sequence is preferably provided in the form of cDNA, is inserted by customary methods familiar to the skilled person into a suitable vector and is introduced into the target cell. The methods of plasmid construction and transformation of the target cells are in no way limiting for the present invention. It is possible to use all methods known to the skilled person and leading to a suitable expression host which can express the desired sequence in a functional manner.

The choice of the vector used for constructing the plasmid is not limiting either, as long as it is possible to obtain a plasmid which enables expression, preferably inducible expression, in the chosen host. A preferred plasmid can be expressed in *E. coli*, preferably in the *E. coli* strain Origami (DE3) (obtainable from Novagen, Madison, Wis., USA). A particularly preferred vector for the plasmid construction for expressing the desired protein is the vector pET15b (Novagen, Madison, Wis., USA) which has suitable cloning cleavage sites for inserting desired sequences. The plasmid pET15b_mPLE constructed from this vector and the preferred esterase sequence represents a plasmid to be used particularly preferably according to the invention in a suitable host organism. This complete construct is depicted in SEQ ID No. 2.

According to the present invention, the host organism comprises a chaperone system which is suitable and able to assist the folding of the expressed heterologous protein to give a functional enzyme with catalytic activity. Chaperones are so-called "folding helper proteins" which are "of assistance" in the correct three-dimensional arrangement of an amino acid sequence to give the "finished" protein, specifically both during expression of the protein and in the correction of "disarrangements", e.g. after the denaturation of proteins. Chaperones are also known as "heat shock proteins" because there is a distinct enhancement of expression thereof in cells after brief exposure to elevated temperatures. Various chaperone systems have been disclosed, and one of the best-investigated systems is the GroEL/GroES system, a bacterial chaperone system in which the two factors GroEL and GroES cooperate closely.

A chaperone system which is preferably used according to the invention is one which brings about the correct folding, leading to an enzymic activity, of heterologous proteins, in particular of mammalian proteins, it being possible to dispense with a post-translational modification, which normally takes place where appropriate in the original cell, of the protein. A chaperone system which is preferably used according to the present invention includes at least GroEL and GroES, it also being possible for other chaperones to be present, but the chaperones Dnak, DnaJ and GrpE are particularly preferably not present. In a preferred embodiment, the chaperone system employed according to the invention can be induced by an initiating stimulus which can easily be applied and which otherwise has no adverse effect on the host cells. Although chaperones can be induced naturally by a heat shock, in most cases this also has an effect on the other conditions of the cells and may lead for example to extensive denaturation of proteins. It is therefore preferred to bring about the induction of the chaperone system for example by adding an inducing substance. Such inducible chaperone systems are known to the skilled person and are commercially available on the market, with polynucleic acid sequences which encode the desired chaperones to be used being provided on plasmids. Induction of the expression of these sequences is achieved by a sequence which is located upstream on the plasmid and which, after addition of an inducing substance, regulates an increase in the expression of the sequences following it. One supplier of chaperone plasmid sets is for example TAKARA BIO Inc., Otsu, Japan. However, it is possible to use any other plasmids from various suppliers which provide chaperone systems which are suitable for use according to the present invention.

The desired chaperone system is preferably likewise introduced into a suitable host organism, e.g. by transformation or transfection of the host cell. It is thus preferred to prepare a transgenic cell which is able, through the introduction of suitable polynucleic acid sequences which code for the desired chaperone system, to provide the desired chaperone system, preferably after induction. However, the information for the desired chaperone system may also already be present in the host cell in its own genome, so that the selection of suitable host cells which provide an appropriate chaperone system is also suitable for the invention. However, the chaperone system should preferably be inducible by a stimulus which is not otherwise disadvantageous. This is the case primarily when plasmids which include the inducible chaperone system as coding sequences are used.

A particularly preferred plasmid to be introduced for the purposes of the present invention into a suitable host is the plasmid pGro7 which is obtainable from TAKARA BIO Inc., Otsu, Japan. However, all other commercially available plasmids which provide the GroEL/GroES system as inducible system are likewise to be regarded as preferred.

A host organism which is rendered, through the introduction of the heterologous polynucleic acid sequence(s), specifically at least the sequence for the enzyme to be expressed and where appropriate, or preferably, the sequences for the chaperone system, capable of expressing the desired protein as functional enzyme with a catalytic activity can be used to synthesize the enzyme or at least a catalytically active fragment thereof and to produce the latter in economically worthwhile quantities.

The present invention therefore likewise relates to a method for producing a catalytically active protein (fragment thereof), preferably a protein with esterase activity as described in detail above, where the protein is expressed by a microorganism into which a polynucleic acid sequence coding for the heterologous protein has been introduced, and which has a, preferably inducible, chaperone system which makes it possible for the enzyme to be provided in its functional form.

All organisms to be used are of course to be cultured and stimulated to expression under culturing conditions which allow growth and expression of the heterologous protein. Suitable culturing conditions are known to every person skilled in the area of microbiology and molecular biology and are generally notified by the distributors of the organisms or of the chaperone or expression systems.

A particularly preferred embodiment of the method is a method for producing the pig liver esterase with SEQ ID No. 5 with coexpression of the chaperones GroEL and GroES in an *E. coli* Origami (DE3) strain. Surprisingly, expression of the active enzyme was achieved in the presence of these two folding helper proteins, although other alternative chaperone systems such as, for example, the chaperones belonging to *E. coli* and induced by ethanol addition (see comparative example 5), or other coexpressed chaperones such as DnaK, DnaJ and GrpE, do not lead to success (see comparative example 6).

It is surprising to the skilled person that equivalent coexpression of the two chaperone systems Dnak, DnaJ, GrpE and GroEL, GroES together with the pig liver esterase in *E. coli* Origami (DE3) leads only to expression in the form of inclusion bodies and not to a detectable activity in *E. coli* crude cell extract (see comparative example 6). It is therefore preferred in every case for the GroEL/GroES chaperone system to be the system which is preferably induced/expressed even if other chaperone systems are present at the same time in the host organism.

Functional expression of eukaryotic proteins in *E. coli* represents a great challenge, especially if the proteins undergo post-translational glycosylation. In the case of the recombinant expression of pig liver esterase in *E. coli*, the use of the specific GroEL, GroES chaperone system apparently compensates for the lack of post-translational glycosylation.

Figure 1:
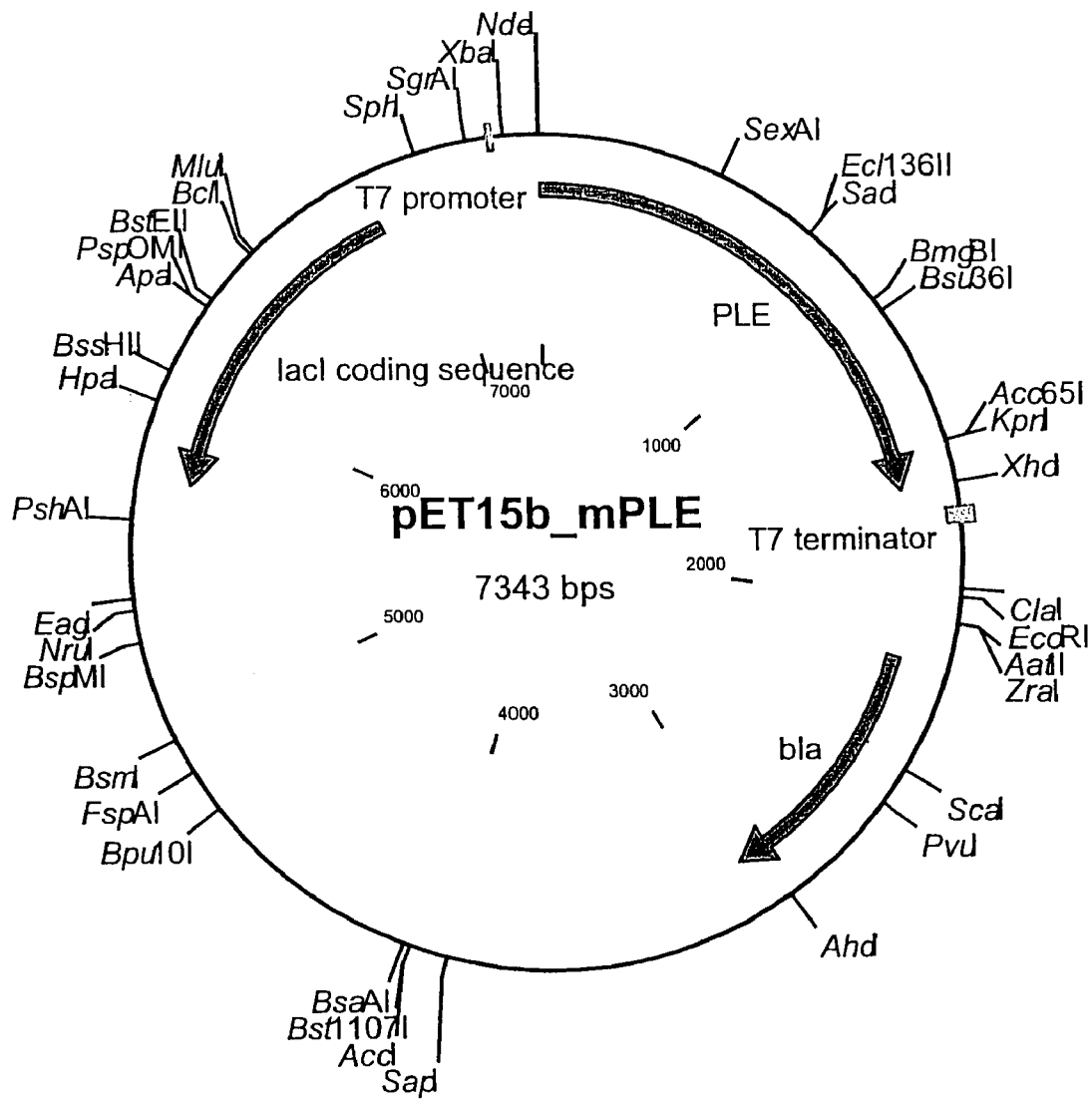
FIG. 1 shows the plasmid map of the plasmid pET15b_Mple.

Some exemplary embodiments are given below to illustrate the invention, but they are not to be regarded as restrictive.

EXAMPLES

General Information, and Microorganisms Media, Vectors and Oligonucleotides Used:

The *Escherichia coli* strains *E. coli* One Shot® TOP10 competent cells (Invitrogen, Carlsbad, Calif., USA) [F-mcrA D(mrr-hsdRMSmcrBC) (F801acZDM15) DlacX74 recA1 deoR araD139 D(ara-leu)7697 galU galK rpsL (StrR) endA1 nupG] or DH5α [supE44ΔlacU169 (Φ80lacZΔM15) hsdR17 recA1 endA1 gyrA96 thi-lrelA1] were used to maintain and replicate the plasmids. The *E. coli* strains Rosetta (DE3) [F-ompT hsdSB(rB-mB-) gal dcm (DE3) pRARE2 (CamR)], Origami (DE3) [Δ(ara-leu)7697 ΔlacX74 ΔphoA PvuII phoR araD139 ahpC galE galK rpsL F' [lac+lacIq pro] (DE3) gor522::Tn10 trxB (KanR, StrR, TetR)4], Rosetta-gami B (DE3) [F-ompT hsdSB(rB-mB-) gal dcm lacY1 aphC (DE3) gor522::Tn10 trxB pRARE2 (CamR, KanR, TetR)], all from Novagen (Madison, Wis., USA), and BL21Star™ (DE3) [F-ompT hsdSB(rB-mB-) gal dcm me131 (DE3)] are used for the expression experiments.

The *E. coli* cells are cultured in Luria Bertani (LB) medium [yeast extract (5 g L$^{-1}$), peptone (10 g L$^{-1}$), NaCl (10 g L$^{-1}$)], to which the necessary antibiotics are added, at various temperatures (20-37° C.).

```
Primer 1 (SEQ ID NO. 3):
5'-GCCATATGGGGCAGCCAGCCTCGCCGCCTG-3'

Primer 2 (SEQ ID NO. 4):
5'-GATCCTCGAGTCACTTTATCTTGGGTGGC-3'
```

The plasmids pG-KJE8, pGro7, pKJE7 were purchased from TAKARA BIO Inc., Otsu, Shiga, Japan, in the form of a chaperone plasmid set. The plasmid pGro7 has a p15A origin of replication and a chloramphenicol resistance. The genes which code for the chaperones GroEL and GroES are located behind an arabinose promoter. Addition of a suitable quantity of arabinose is followed by expression of the folding helpers GroEL and GroES [Nishihara, K.; et al., Appl. Environ. Microbiol. (1998), 64, 1694-1699].

The vector pET15b was purchased from Novagen. The vector pET15b has a ColE1 origin of replication and an ampicillin resistance. The vector possesses a so-called multiple cloning site into which the gene to be expressed is cloned. These genes are then under the control of the strong T7 promoter [The pET System Manual, 11$^{th}$ edition, Novagen (TB055)].

General Information: DNA Recombination and Transformation

Unless mentioned otherwise, standard methods according to Sambrook, J. and Russell, D. W., Molecular Cloning, A Laboratory Manual, (2001), 3$^{rd}$ ed., Cold Spring Harbour, N.Y., were used.

A QiAprep spin miniprep kit, a plasmid midi kit or a QIAquick gel extraction kit (Qiagen, Hilden, Germany) was used for plasmid and DNA extraction. The restriction enzymes employed were used in accordance with the respective manufacturer's information. The DNA sequencing was carried out by MWG-Biotech (Ebersberg, Germany). A standard protocol of Chung, C. T., et al. (1989) Proc. Natl. Acad. Sci. USA. 86, 2172-2175, was used for the preparation transformation of competent *E. coli* cells.

SDS Polyacrylamide Gel Electrophoresis and Zymogram

20 µl of commercially available pig liver carboxylesterase purchased from Sigma-Aldrich (100 U according to pNPA assay), dissolved in 2 ml as control and 20 µl of the cell lysate of the *E. coli* cultures were mixed with 10 µl of a 2×SDS sample buffer. After the solution had been heated at 95° C. for 5 min, the proteins were separated on a 12.5% polyacrylamide gel with 4% stacking gel. The samples were stained with Coomassie Brilliant Blue R250 to detect proteins.

For the esterase activity determination, the proteins fractionated in the polyacrylamide gel were renatured in a Triton X-100 solution (0.5% in 0.1 M Tris/HCl pH 7.5) for 1 hour. The gel was then mixed with a 1:1 mixture of solution A (20 mg of α-naphthyl acetate dissolved in 5 ml of acetone and subsequent addition of 50 ml of 0.1 M Tris/HCl pH 7.5) and solution B (50 mg Fast Red TR salt dissolved in 50 ml of 0.1 M Tris/HCl, pH 7.5). In the presence of hydrolytic lipase or esterase activity, a red α-naphthyl form of the Fast Red is formed (Krebsfänger, N., et al., (1998) Enzym Microb. Technol., 22, 641-646).

Determination of the Esterase Activity

The esterase activity was determined by photometry in a sodium phosphate buffer (50 mM, pH 7.5). The substrate used was p-nitrophenyl acetate (10 mM dissolved in DMSO). The liberated amount of p-nitrophenol was determined at 410 nm (e=12.36×10$^3$ M$^{-1}$cm$^{-1}$) at room temperature. The enzymic activity was additionally determined with variation of the pH. A unit U is defined as an esterase activity with which 1 µmol of p-nitrophenol is liberated per minute under assay conditions.

Determination of the Protein Content in the *E. coli* Crude Cell Extract

The protein assay from Bio-Rad was used for Bradford determination of the protein concentrations in solution. The assay is based on the use of the dye Coomassie Brilliant Blue G-250 which binds with high specificity to proteins. In an acidic solution of Coomassie Brilliant Blue G-250 bound to proteins there is a shift in the absorption maximum of the unbound dye from 465 nm to 595 nm [Bradford, M. M., Anal. Biochem. (1976), 72, 248-254]. Protein quantities in the range 1-20 µg can be determined with this method.

Cell Disruption with Ultrasound 1 g of wet cell mass is resuspended in 10 ml of sodium phosphate buffer (50 mM, pH 7.5) and treated with ultrasound on ice for 3×1 min with a one minute pause in each case (80 W, pulses 35% s$^{-1}$). Centrifugation is then carried out at 3300 g and 4° C. for 20 min in order to remove cell detritus. The clear supernatant is used for further experiments.

Construction of the Expression Vector

The sequence SEQ ID No. 1 coding for pig liver esterase (PLE) was amplified by PCR with primers 1 and 2 and, during this, an NdeI cleavage site was introduced at the 5' end and an XhoI cleavage site at the 3' end. The plasmid pCYTEX-PLE which was used in earlier studies on the cloning of pig liver esterase [Lange, S. et al., ChemBioChem (2001), 2, 576-582] was used as template. The PCR amplicon was treated with NdeI and XhoI and then introduced under standard conditions into the vector pET15b which had been treated in the same way. The construct obtained in this way, pET15bmPLE (see FIG. 1 and SEQ ID No. 2) was then transformed under standard conditions into the various *E. coli* expression strains.

Comparative Example 1

Expression of Recombinant PLE in *Escherichia coli* BL21Star™ (DE3)

The plasmid pET15bmPLE was transformed under standard conditions into *E. coli* BL21 Star™. Single colonies were then cultured in 5 ml of LB medium mixed with ampicillin (100 µg/ml) at 30° C. overnight. The next day, the preculture was diluted in LB medium mixed with 100 µg/ml ampicillin to an $OD_{600}$ of 0.05 and then cultured at 30° C. and 200 rpm until the $OD_{600}$ was 1, and then expression was induced by adding IPTG to a final concentration of 100 μmol/1.5 ml samples were taken after 2 and 24 hours and, after cell disruption with ultrasound, the samples were investigated by SDS-PAGE and assayed for activity with the activity assay described above. No soluble protein corresponding to PLE was detected in the SDS-PAGE to indicate expression in the cytosol; on the contrary, only inclusion bodies were detected. No activity was detectable in the activity assay.

Comparative Example 2

Expression of recombinant PLE in *Escherichia coli* Rosetta (DE3)

The plasmid pET15bmPLE was transformed under standard conditions into *E. coli* Rosetta (DE3). Single colonies were then cultured in 5 ml of LB medium mixed with ampicillin (100 μg/ml) at 30° C. overnight. The next day, the preculture was diluted in LB medium mixed with 100 μg/ml ampicillin to an $OD_{600}$ of 0.05 and then cultured at 30° C. and 200 rpm until the $OD_{600}$ was 1, and then expression was induced by adding IPTG to a final concentration of 100 μmol/1.5 ml samples were taken after 2 and 24 hours and, after cell disruption with ultrasound, the samples were investigated by SDS-PAGE and assayed for activity with the activity assay described above. No soluble protein corresponding to PLE was detected in the SDS-PAGE; on the contrary, only inclusion bodies were detected. No activity was detectable in the activity assay.

Comparative Example 3

Expression of Recombinant PLE in *Escherichia coli* Origami (DE3)

The plasmid pET15bmPLE was transformed under standard conditions into *E. coli* Origami (DE3). Single colonies were then cultured in 5 ml of LB medium mixed with ampicillin (100 μg/ml) at 30° C. overnight. The next day, the preculture was diluted in LB medium mixed with 100 μg/ml ampicillin to an $OD_{600}$ of 0.05 and then cultured at 30° C. and 200 rpm until the $OD_{600}$ was 1, and then expression was induced by adding IPTG to a final concentration of 100 μmol/1.5 ml samples were taken after 2 and 24 hours and, after cell disruption with ultrasound, the samples were investigated by SDS-PAGE and assayed for activity with the activity assay described above. No soluble protein corresponding to PLE was detected in the SDS-PAGE; on the contrary, only inclusion bodies were detected. No activity was detectable in the activity assay.

Comparative Example 4

Expression of Recombinant PLE in *Escherichia coli* Rosetta-Gami B (DE3)

The plasmid pET15bmPLE was transformed under standard conditions into *E. coli* Rosetta-gami B (DE3). Single colonies were then cultured in 5 ml of LB medium mixed with ampicillin (100 μg/ml) at 30° C. overnight. The next day, the preculture was diluted in LB medium mixed with 100 μg/ml ampicillin to an $OD_{600}$ of 0.05 and then cultured at 30° C. and 200 rpm until the $OD_{600}$ was 1, and then expression was induced by adding IPTG to a final concentration of 100 μmol/1.5 ml samples were taken after 2 and 24 hours and, after cell disruption with ultrasound, the samples were investigated by SDS-PAGE and assayed for activity with the activity assay described above. No soluble protein corresponding to PLE was detected in the SDS-PAGE; on the contrary, only inclusion bodies were detected. A small, scarcely quantifiable activity was detectable in the activity assay after 2 h, but was no longer detectable after 24 hours.

Comparative Example 5

Expression of recombinant PLE in *Escherichia coli* Origami (DE3) with Addition of Ethanol to Induce Chaperones Belonging to *E. coli*

The plasmid pET15bmPLE was transformed under standard conditions into *E. coli* Origami (DE3). Single colonies were then cultured in 5 ml of LB medium mixed with ampicillin (100 μg/ml) at 30° C. overnight. The next day, the preculture was diluted in LB medium mixed with 100 μg/ml ampicillin and 3% (v/v) ethanol to induce the chaperones belonging to *E. coli* to an $OD_{600}$ of 0.05 and then cultured at 30° C. and 200 rpm until the $OD_{600}$ was 1, and then expression was induced by adding IPTG to a final concentration of 100 μmol/1.5 ml samples were taken after 2 and 24 hours and, after cell disruption with ultrasound, the samples were investigated by SDS-PAGE and assayed for activity with the activity assay described above. No soluble protein corresponding to PLE was detected in the SDS-PAGE; on the contrary, only inclusion bodies were detected. No activity was detectable in the activity assay.

Comparative Example 6

Expression of Recombinant PLE in *Escherichia coli* Origami (DE3) with Coexpression of the Chaperones Dnak, DnaJ, GrpE and GroEL, GroES The plasmid pET15bmPLE was transformed under standard conditions into *E. coli* Origami (DE3) and then the plasmid pKJE7 was transformed into the strain resulting therefrom. Single colonies resulting therefrom were cultured in 5 ml of LB medium mixed with ampicillin (50 μg/ml) and chloramphenicol (20 μg/ml) at 30° C. overnight. The next day, the preculture was diluted in LB medium mixed with 100 μg/ml ampicillin and 50 μg/ml chloramphenicol to an $OD_{600}$ of 0.05. Immediately thereafter, expression of the chaperones Dnak, DnaJ, GrpE, GroEL and GroES was induced by adding arabinose to a final concentration of 1 mg/ml. Culturing was continued at 30° C. and 200 rpm until the $OD_{600}$ was 0.5, and expression of pig liver esterase was induced by adding IPTG to a final concentration of 40 μmol/1.5 ml samples were taken after 2 and 24 hours and, after cell disruption with ultrasound, the samples were investigated by SDS-PAGE and assayed for activity with the activity assay described above. No soluble protein corresponding to PLE was detected in the SDS-PAGE; on the contrary, only inclusion bodies were detected. No activity was detectable in the activity assay.

Expression of Recombinant PLE in *Escherichia coli* Origami (DE3) with Coexpression of the Chaperones GroEL and GroES The plasmid pET15bmPLE was transformed under standard conditions into *E. coli* Origami (DE3) and then the plasmid pGro7 was transformed into the strain resulting therefrom. Single colonies resulting therefrom were cultured in 5 ml of LB medium mixed with ampicillin (50 μg/ml) and chloramphenicol (20 μg/ml) at 30° C. overnight. The next day, the preculture was diluted in LB medium mixed with 100 μg/ml ampicillin and 50 μg/ml chloramphenicol to an $OD_{600}$ of 0.05. Immediately thereafter, expression of the chaperones GroEL and GroES was induced by adding arabinose to a final concentration of 1 mg/ml. Culturing was continued at 30° C. and 200 rpm until the $OD_{600}$ was 0.5, and expression of pig liver esterase was induced by adding IPTG to a final concentration of 40 μmol/1.5 ml samples were taken after 2 and 24 hours and, after cell disruption with ultrasound, the samples were investigated by SDS-PAGE and assayed for activity with the activity assay described above. In the SDS-PAGE, a soluble protein corresponding to PLE was mainly detected, and no inclusion bodies were detectable. In the activity assay, an activity was detectable with the activity assay described above. It amounted to 9.94 Upper ml of crude cell extract and the total protein content was 15.7 mg/ml determined by the Bradford method.

TABLE 1

Expression, inclusion body formation and volumetric activities

| E. coli strain | PLE expression | Activity* volumetric [U/ml] | IB** |
|---|---|---|---|
| BL21Star ™ (DE3) (pET15bmPLE) | yes | 0 | yes |
| Rosetta (DE3) (pET15bmPLE) | yes | 0 | yes |
| Origami (DE3) (pET15bmPLE) | yes | 0 | yes |
| Rosetta-gami B (DE3) (pET15bmPLE) | yes | <0.2 | yes |
| Origami (DE3) (pET15bmPLE, pKJE7) | yes | 0 | yes |
| Origami (DE3) (pET15bmPLE, pG-KJE8) | yes | 0 | yes |
| Origami (DE3) (pET15bmPLE, pGro7) | yes | 9.94 | n.d.*** |

*Units based on the pNPA assay
**IB inclusion bodies
***n.d. not detectable

Incorporation by Reference

Each document, patent, patent application or patent publication cited by or referred to in this disclosure is incorporated by reference in its entirety. However, no admission is made that any such reference constitutes prior art and the right to challenge the accuracy and pertinency of the cited documents is reserved. Specifically, the structural description of polynucleotide and amino acid sequences and chaperonin proteins (e.g., by sequence), and taxonomic, phenotypic or genotypic description of host cells useful for expression of the enzymes of the invention, are specifically incorporated by reference to the sequences and cell lines described by the cited references.

The invention claimed is:

1. An isolated microorganism comprising at least one copy of the polynucleic acid sequence as set forth in SEQ ID NO: 1 or a codon degenerate sequence thereof which is adapted to the host-specific codon usage, and a chaperone system which assists the functional expression of the protein encoded by the polynucleic acid sequence in the form of an active enzyme.

2. The microorganism according to claim 1, where the microorganism is an *E. coli* strain.

3. The microorganism according to claim 1, where the polynucleotide sequence encodes an esterase.

4. The microorganism according to claim 1, where the sequence is a cDNA sequence from the pig genome.

5. The microorganism according to claim 1, where the chaperone system includes the chaperones GroEL and GroES.

6. The microorganism according to claim 5, where the expression of the coding sequences for the chaperones GroEL and GroES is inducible.

7. The microorganism according to claim 5, where the microorganism is transgenic in relation to the coding sequences for the chaperones GroEL and GroES.

8. The microorganism according to claim 5, where the chaperone system does not include the chaperones Dnak, DnaJ and GrpE.

9. The microorganism according to claim 1, where the microorganism comprises the polynucleic acid sequence of SEQ ID NO 2.

10. The microorganism of claim 1, wherein said polynucleic acid sequence encodes a stereoselective esterase.

11. The microorganism of claim 10, where the polynucleotide sequence encodes the amino acid sepuence of SEQ ID NO: 5.

* * * * *

SEQUENCE LISTING

```
<160> NUMBER OF SEQ ID NOS: 5

<210> SEQ ID NO 1
<211> LENGTH: 1638
<212> TYPE: DNA
<213> ORGANISM: Sus

<400> SEQUENCE: 1
atggggcagc cagcctcgcc gcctgttgtg gacactgccc agggccgagt cctggggaag      60
tacgtcagct tagaaggcct ggcacagccg gtggccgtct tcctgggagt cccttttgcc     120
aagcccccct tcggatcctt gaggtttgct ccgccgcagc ctgcagaacc atggagcttc     180
gtgaagaaca ccacctccta ccctcccatg tgctgccagg acccagtagt ggagcagatg     240
acctcagatc tatttaccaa cggaaggag aggctcactc tggagttttc tgaagactgt      300
ctctacctaa atatttacac ccctgctgac ctgacaaaga ggggcagact gccggtgatg     360
gtgtggatcc acggaggagg cctggtgttg ggcgggcac caatgtatga tggggtggtg      420
cttgctgcgc atgaaaacgt ggtggtggtg gccatccagt accgcctggg catctgggga     480
ttcttcagca caggggatga acacagccgg ggcaactggg gtcacttgga ccaggtggcc     540
gcactgcact gggtccagga gaacatcgcc aactttggag gcgacccagg ctctgtgacc     600
atctttggag agtcagcagg aggggaaagt gtctctgttc tggtgttgtc tcccttggcc     660
aagaacctct tccaccgggc catctctgag agtggcgtgg ccctcactgt tgccctggtc     720
aggaaggaca tgaaggctgc agctaagcaa attgctgtcc ttgctgggtg taaaaccacc     780
acctcggctg tctttgttca ctgcctgcgc cagaagtcgg aggacgagct cttggactta     840
acgctgaaga tgaatttttt aactcttgat tttcatggag accaaagaga gagccatccc     900
ttcctgccca ctgtggtgga tggagtgctg ctgcccaaga tgcctgaaga gattctggct     960
```

| | |
|---|---|
| gagaaggatt tcaacactgt cccctacatc gtgggaatca acaagcaaga gtttggctgg | 1020 |
| cttctgccaa cgatgatggg cttcccctc tctgaaggca agctggacca gaagacggcc | 1080 |
| acgtcactcc tgtggaagtc ctaccccatc gctaacatcc ctgaggaact gactccagtg | 1140 |
| gccactgaca agtatttggg ggggacagac gaccccgtca aaagaaaga cctgttcctg | 1200 |
| gacttgatgg gggatgtggt gtttggtgtc ccatctgtga cggtggcccg tcaacacaga | 1260 |
| gatgcaggag cccccaccta catgtatgag tttcagtatc gcccaagctt ctcatcggac | 1320 |
| aagaaaccca agacggtgat cggggaccac ggggatgaga tcttctccgt ctttggtttt | 1380 |
| ccactgttaa aaggcgatgc cccagaagag gaggtcagtc tcagcaagac ggtgatgaaa | 1440 |
| ttctgggcca actttgctcg cagtgggaac cccaatgggg aggggctgcc ccattggccg | 1500 |
| atgtacgacc aggaagaagg gtaccttcag atcggcgtca acaccaggc agccaagagg | 1560 |
| ctgaaaggtg aagaagtggc cttctggaac gatctcctgt ccaaggaggc agcaaagaag | 1620 |
| ccacccaaga taaagtga | 1638 |

<210> SEQ ID NO 2
<211> LENGTH: 7343
<212> TYPE: DNA
<213> ORGANISM: Artificial Sequence
<220> FEATURE:
<223> OTHER INFORMATION: DNA construct: plasmid

<400> SEQUENCE: 2

| | |
|---|---|
| tatggggcag ccagcctcgc cgcctgttgt ggacactgcc cagggccgag tcctggggaa | 60 |
| gtacgtcagc ttagaaggcc tggcacagcc ggtggccgtc ttcctgggag tcccttttgc | 120 |
| caagccccct ctcggatcct tgaggtttgc tccgccgcag cctgcagaac catggagctt | 180 |
| cgtgaagaac accacctcct accctcccat gtgctgccag gacccagtag tggagcagat | 240 |
| gacctcagat ctatttacca acggaaagga gaggctcact ctggagtttt ctgaagactg | 300 |
| tctctaccta aatatttaca cccctgctga cctgacaaag aggggcagac tgccggtgat | 360 |
| ggtgtggatc cacggaggag gcctggtgtt gggcggggca ccaatgtatg atggggtggt | 420 |
| gcttgctgcg catgaaaacg tggtggtggt ggccatccag taccgcctgg gcatctgggg | 480 |
| attcttcagc acaggggatg aacacagccg gggcaactgg ggtcacttgg accaggtggc | 540 |
| cgcactgcac tgggtccagg agaacatcgc caactttgga ggcgacccag gctctgtgac | 600 |
| catctttgga gagtcagcag aggggaaag tgtctctgtt ctggtgttgt ctcccttggc | 660 |
| caagaacctc ttccaccggg ccatctctga gagtggcgtg gccctcactg ttgccctggt | 720 |
| caggaaggac atgaaggctg cagctaagca aattgctgtc cttgctgggt gtaaaaccac | 780 |
| cacctcgggc gtctttgttc actgcctgcg ccagaagtcg gaggacgagc tcttggactt | 840 |
| aacgctgaag atgaaatttt taactcttga ttttcatgga gaccaaagag agagccatcc | 900 |
| cttcctgccc actgtggtgg atggagtgct gctgccaag atgcctgaag agattctggc | 960 |
| tgagaaggat ttcaacactg tcccctacat cgtgggaatc aacaagcaag agtttggctg | 1020 |
| gcttctgcca cgatgatgg gcttcccct tctgaaggc aagctggacc agaagacggc | 1080 |
| cacgtcactc ctgtggaagt cctaccccat cgctaacatc cctgaggaac tgactccagt | 1140 |
| ggccactgac aagtatttgg ggggacaga cgacccgtc aaaagaaag acctgttcct | 1200 |
| ggacttgatg gggatgtgg tgtttggtgt cccatctgtg acggtggccc gtcaacacag | 1260 |
| agatgcagga gcccccacct acatgtatga gtttcagtat cgcccaagct tctcatcgga | 1320 |
| caagaaaccc aagacggtga tcggggacca cggggatgag atcttctccg tctttggttt | 1380 |

-continued

```
tccactgtta aaaggcgatg ccccagaaga ggaggtcagt ctcagcaaga cggtgatgaa   1440
attctgggcc aactttgctc gcagtgggaa ccccaatggg gaggggctgc cccattggcc   1500
gatgtacgac caggaagaag ggtaccttca gatcggcgtc aacacccagg cagccaagag   1560
gctgaaaggt gaagaagtgg ccttctggaa cgatctcctg tccaaggagg cagcaaagaa   1620
gccacccaag ataaagtgac tcgaggatcc ggctgctaac aaagcccgaa aggaagctga   1680
gttggctgct gccaccgctg agcaataact agcataaccc cttggggcct ctaaacgggt   1740
cttgaggggt ttttgctga aggaggaac tatatccgga tatcccgcaa gaggcccggc    1800
agtaccggca taaccaagcc tatgcctaca gcatccaggg tgacggtgcc gaggatgacg   1860
atgagcgcat tgttagattt catacacggt gcctgactgc gttagcaatt taactgtgat   1920
aaactaccgc attaaagctt atcgatgata agctgtcaaa catgagaatt cttgaagacg   1980
aaagggcctc gtgatacgcc tatttttata ggttaatgtc atgataataa tggtttctta   2040
gacgtcaggt ggcacttttc ggggaaatgt gcgcggaacc cctatttgtt tatttttcta   2100
aatacattca aatatgtatc cgctcatgag acaataaccc tgataaatgc ttcaataata   2160
ttgaaaaagg aagagtatga gtattcaaca tttccgtgtc gcccttattc ccttttttgc   2220
ggcattttgc cttcctgttt ttgctcaccc agaaacgctg gtgaaagtaa aagatgctga   2280
agatcagttg ggtgcacgag tgggttacat cgaactggat ctcaacagcg gtaagatcct   2340
tgagagtttt cgccccgaag aacgttttcc aatgatgagc acttttaaag ttctgctatg   2400
tggcgcggta ttatcccgtg ttgacgccgg gcaagagcaa ctcggtcgcc gcatacacta   2460
ttctcagaat gacttggttg agtactcacc agtcacagaa aagcatctta cggatggcat   2520
gacagtaaga gaattatgca gtgctgccat aaccatgagt gataacactg cggccaactt   2580
acttctgaca acgatcggag gaccgaagga gctaaccgct tttttgcaca acatggggga   2640
tcatgtaact cgccttgatc gttgggaacc ggagctgaat gaagccatac caaacgacga   2700
gcgtgacacc acgatgcctg cagcaatggc aacaacgttg cgcaaactat taactggcga   2760
actacttact ctagcttccc ggcaacaatt aatagactgg atggaggcgg ataaagttgc   2820
aggaccactt ctgcgctcgg cccttccggc tggctggttt attgctgata aatctggagc   2880
cggtgagcgt gggtctcgcg gtatcattgc agcactgggg ccagatggta agccctcccg   2940
tatcgtagtt atctacacga cggggagtca ggcaactatg gatgaacgaa atagacagat   3000
cgctgagata ggtgcctcac tgattaagca ttggtaactg tcagaccaag tttactcata   3060
tatactttag attgatttaa aacttcattt ttaatttaaa aggatctagg tgaagatcct   3120
ttttgataat ctcatgacca aaatccctta acgtgagttt tcgttccact gagcgtcaga   3180
ccccgtagaa aagatcaaag gatcttcttg agatcctttt tttctgcgcg taatctgctg   3240
cttgcaaaca aaaaaaccac cgctaccagc ggtggtttgt ttgccggatc aagagctacc   3300
aactcttttt ccgaaggtaa ctggcttcag cagagcgcag ataccaaata ctgtccttct   3360
agtgtagccg tagttaggcc accacttcaa gaactctgta gcaccgccta catacctcgc   3420
tctgctaatc ctgttaccag tggctgctgc cagtggcgat aagtcgtgtc ttaccgggtt   3480
ggactcaaga cgatagttac cggataaggc gcagcggtcg ggctgaacgg ggggttcgtg   3540
cacacagccc agcttggagc gaacgaccta caccgaactg agatacctac agcgtgagct   3600
atgagaaagc gccacgcttc ccgaagggag aaaggcggac aggtatccgg taagcggcag   3660
ggtcggaaca ggagagcgca cgagggagct tccaggggga aacgcctggt atctttatag   3720
tcctgtcggg tttcgccacc tctgacttga gcgtcgattt ttgtgatgct cgtcaggggg   3780
```

-continued

```
gcggagccta tggaaaaacg ccagcaacgc ggccttttta cggttcctgg ccttttgctg    3840
gccttttgct cacatgttct ttcctgcgtt atccctgat  tctgtggata accgtattac    3900
cgcctttgag tgagctgata ccgctcgccg cagccgaacg accgagcgca gcgagtcagt    3960
gagcgaggaa gcggaagagc gcctgatgcg gtattttctc cttacgcatc tgtgcggtat    4020
ttcacaccgc atatatggtg cactctcagt acaatctgct ctgatgccgc atagttaagc    4080
cagtatacac tccgctatcg ctacgtgact gggtcatggc tgcgcccga  cacccgccaa    4140
cacccgctga cgcgccctga cgggcttgtc tgctcccggc atccgcttac agacaagctg    4200
tgaccgtctc cgggagctgc atgtgtcaga ggttttcacc gtcatcaccg aaacgcgcga    4260
ggcagctgcg gtaaagctca tcagcgtggt cgtgaagcga ttcacagatg tctgcctgtt    4320
catccgcgtc cagctcgttg agtttctcca gaagcgttaa tgtctggctt ctgataaagc    4380
gggccatgtt aagggcggtt ttttcctgtt tggtcactga tgcctccgtg taagggggat    4440
ttctgttcat gggggtaatg ataccgatga aacgagagag gatgctcacg atacgggtta    4500
ctgatgatga acatgcccgg ttactggaac gttgtgaggg taaacaactg gcggtatgga    4560
tgcggcggga ccagagaaaa atcactcagg gtcaatgcca gcgcttcgtt aatacagatg    4620
taggtgttcc acagggtagc cagcagcatc ctgcgatgca gatccggaac ataatggtgc    4680
agggcgctga cttccgcgtt tccagacttt acgaaacacg gaaaccgaag accattcatg    4740
ttgttgctca ggtcgcagac gttttgcagc agcagtcgct tcacgttcgc tcgcgtatcg    4800
gtgattcatt ctgctaacca gtaaggcaac cccgccagcc tagccgggtc ctcaacgaca    4860
ggagcacgat catgcgcacc cgtggccagg acccaacgct gcccgagatg cgccgcgtgc    4920
ggctgctgga gatggcggac gcgatggata tgttctgcca agggttggtt tgcgcattca    4980
cagttctccg caagaattga ttggctccaa ttcttggagt ggtgaatccg ttagcgaggt    5040
gccgccggct tccattcagg tcgaggtggc ccggctccat gcaccgcgac gcaacgcggg    5100
gaggcagaca aggtataggg cggcgcctac aatccatgcc aacccgttcc atgtgctcgc    5160
cgaggcggca taaatcgccg tgacgatcag cggtccagtg atcgaagtta ggctggtaag    5220
agccgcgagc gatccttgaa gctgtccctg atggtcgtca tctacctgcc tggacagcat    5280
ggcctgcaac gcgggcatcc cgatgccgcc ggaagcgaga agaatcataa tggggaaggc    5340
catccagcct cgcgtcgcga acgccagcaa gacgtagccc agcgcgtcgg ccgccatgcc    5400
ggcgataatg gcctgcttct cgccgaaacg tttggtggcg ggaccagtga cgaaggcttg    5460
agcgagggcg tgcaagattc cgaataccgc aagcgacagg ccgatcatcg tcgcgctcca    5520
gcgaaagcgg tcctcgccga aaatgaccca gagcgctgcc ggcacctgtc ctacgagttg    5580
catgataaag aagacagtca taagtgcggc gacgatagtc atgccccgcg cccaccggaa    5640
ggagctgact gggttgaagg ctctcaaggg catcggtcga gatcccggtg cctaatgagt    5700
gagctaactt acattaattg cgttgcgctc actgcccgct ttccagtcgg gaaacctgtc    5760
gtgccagctg cattaatgaa tcggccaacg cgcggggaga ggcggtttgc gtattgggcg    5820
ccagggtggt ttttcttttc accagtgaga cgggcaacag ctgattgccc ttcaccgcct    5880
ggccctgaga gagttgcagc aagcggtcca cgctggtttg ccccagcagg cgaaaatcct    5940
gtttgatggt ggttaacggc gggatataac atgagctgtc ttcggtatcg tcgtatccca    6000
ctaccgagat atccgcacca acgcgcagcc cggactcggt aatggcgcgc attgcgccca    6060
gcgccatctg atcgttggca accagcatcg cagtgggaac gatgccctca ttcagcattt    6120
gcatggtttg ttgaaaaccg gacatggcac tccagtcgcc ttcccgttcc gctatcggct    6180
```

-continued

```
gaatttgatt gcgagtgaga tatttatgcc agccagccag acgcagacgc gccgagacag    6240
aacttaatgg gcccgctaac agcgcgattt gctggtgacc caatgcgacc agatgctcca    6300
cgcccagtcg cgtaccgtct tcatgggaga aaataatact gttgatgggt gtctggtcag    6360
agacatcaag aaataacgcc ggaacattag tgcaggcagc ttccacagca atggcatcct    6420
ggtcatccag cggatagtta atgatcagcc cactgacgcg ttgcgcgaga agattgtgca    6480
ccgccgcttt acaggcttcg acgccgcttc gttctaccat cgacaccacc acgctggcac    6540
ccagttgatc ggcgcgagat ttaatcgccg cgacaatttg cgacggcgcg tgcagggcca    6600
gactggaggt ggcaacgcca atcagcaacg actgtttgcc cgccagttgt tgtgccacgc    6660
ggttgggaat gtaattcagc tccgccatcg ccgcttccac ttttccccgc gttttcgcag    6720
aaacgtggct ggcctggttc accacgcggg aaacggtctg ataagagaca ccggcatact    6780
ctgcgacatc gtataacgtt actggtttca cattcaccac cctgaattga ctctcttccg    6840
ggcgctatca tgccataccg cgaaaggttt tgcgccattc gatggtgtcc gggatctcga    6900
cgctctccct tatgcgactc ctgcattagg aagcagccca gtagtaggtt gaggccgttg    6960
agcaccgccg ccgcaaggaa tggtgcatgc aaggagatgg cgcccaacag tcccccggcc    7020
acggggcctg ccaccatacc cacgccgaaa caagcgctca tgagcccgaa gtggcgagcc    7080
cgatcttccc catcggtgat gtcggcgata taggcgccag caaccgcacc tgtgcgccg     7140 gtgatgccgg ccacgatgcg tccggcgtag aggatcgaga tctcgatccc gcgaaattaa    7200
tacgactcac tatagggaa ttgtgagcgg ataacaattc ccctctagaa ataatttgt      7260 ttaactttaa gaaggagata taccatgggc agcagccatc atcatcatca tcacagcagc    7320
ggcctggtgc cgcgcggcag cca                                            7343
```

```
<210> SEQ ID NO 3
<211> LENGTH: 30
<212> TYPE: DNA
<213> ORGANISM: Artificial Sequence
<220> FEATURE:
<223> OTHER INFORMATION: Synthetic DNA: primer

<400> SEQUENCE: 3
gccatatggg gcagccagcc tcgccgcctg                                         30

<210> SEQ ID NO 4
<211> LENGTH: 29
<212> TYPE: DNA
<213> ORGANISM: Artificial Sequence
<220> FEATURE:
<223> OTHER INFORMATION: Synthetic DNA: primer

<400> SEQUENCE: 4
gatcctcgag tcactttatc ttgggtggc                                          29

<210> SEQ ID NO 5
<211> LENGTH: 545
<212> TYPE: PRT
<213> ORGANISM: Sus

<400> SEQUENCE: 5

Met Gly Gln Pro Ala Ser Pro Val Val Asp Thr Ala Gln Gly Arg
  1               5                  10                  15

Val Leu Gly Lys Tyr Val Ser Leu Glu Gly Leu Ala Gln Pro Val Ala
                 20                  25                  30

Val Phe Leu Gly Val Pro Phe Ala Lys Pro Pro Leu Gly Ser Leu Arg
             35                  40                  45
```

```
Phe Ala Pro Pro Gln Pro Ala Glu Pro Trp Ser Phe Val Lys Asn Thr
        50                  55                  60

Thr Ser Tyr Pro Pro Met Cys Cys Gln Asp Pro Val Val Glu Gln Met
65              70                  75                      80

Thr Ser Asp Leu Phe Thr Asn Gly Lys Glu Arg Leu Thr Leu Glu Phe
                    85                  90                  95

Ser Glu Asp Cys Leu Tyr Leu Asn Ile Tyr Thr Pro Ala Asp Leu Thr
                100                 105             110

Lys Arg Gly Arg Leu Pro Val Met Val Trp Ile His Gly Gly Gly Leu
            115                 120                 125

Val Leu Gly Gly Ala Pro Met Tyr Asp Gly Val Val Leu Ala Ala His
        130                 135                 140

Glu Asn Val Val Val Ala Ile Gln Tyr Arg Leu Gly Ile Trp Gly
145                 150                 155                 160

Phe Phe Ser Thr Gly Asp Glu His Ser Arg Gly Asn Trp Gly His Leu
                165                 170                 175

Asp Gln Val Ala Ala Leu His Trp Val Gln Glu Asn Ile Ala Asn Phe
            180                 185                 190

Gly Gly Asp Pro Gly Ser Val Thr Ile Phe Gly Glu Ser Ala Gly Gly
        195                 200                 205

Glu Ser Val Ser Val Leu Val Leu Ser Pro Leu Ala Lys Asn Leu Phe
210                 215                 220

His Arg Ala Ile Ser Glu Ser Gly Val Ala Leu Thr Val Ala Leu Val
225                 230                 235                 240

Arg Lys Asp Met Lys Ala Ala Lys Gln Ile Ala Val Leu Ala Gly
                245                 250                 255

Cys Lys Thr Thr Thr Ser Ala Val Phe Val His Cys Leu Arg Gln Lys
                260                 265                 270

Ser Glu Asp Glu Leu Leu Asp Leu Thr Leu Lys Met Lys Phe Leu Thr
            275                 280                 285

Leu Asp Phe His Gly Asp Gln Arg Glu Ser His Pro Phe Leu Pro Thr
        290                 295                 300

Val Val Asp Gly Val Leu Leu Pro Lys Met Pro Glu Glu Ile Leu Ala
305                 310                 315                 320

Glu Lys Asp Phe Asn Thr Val Pro Tyr Ile Val Gly Ile Asn Lys Gln
                325                 330                 335

Glu Phe Gly Trp Leu Leu Pro Thr Met Met Gly Phe Pro Leu Ser Glu
            340                 345                 350

Gly Lys Leu Asp Gln Lys Thr Ala Thr Ser Leu Leu Trp Lys Ser Tyr
        355                 360                 365

Pro Ile Ala Asn Ile Pro Glu Glu Leu Thr Pro Val Ala Thr Asp Lys
370                 375                 380

Tyr Leu Gly Gly Thr Asp Asp Pro Val Lys Lys Asp Leu Phe Leu
385                 390                 395                 400

Asp Leu Met Gly Asp Val Val Phe Gly Val Pro Ser Val Thr Val Ala
            405                 410                 415

Arg Gln His Arg Asp Ala Gly Ala Pro Thr Tyr Met Tyr Glu Phe Gln
        420                 425                 430

Tyr Arg Pro Ser Phe Ser Ser Asp Lys Lys Pro Lys Thr Val Ile Gly
            435                 440                 445

Asp His Gly Asp Glu Ile Phe Ser Val Phe Gly Phe Pro Leu Leu Lys
        450                 455                 460

Gly Asp Ala Pro Glu Glu Glu Val Ser Leu Ser Lys Thr Val Met Lys
```

-continued

```
465                 470                475                480

Phe Trp Ala Asn Phe Ala Arg Ser Gly Asn Pro Asn Gly Glu Gly Leu
                485                 490                 495

Pro His Trp Pro Met Tyr Asp Gln Glu Glu Gly Tyr Leu Gln Ile Gly
            500                 505                 510

Val Asn Thr Gln Ala Ala Lys Arg Leu Lys Gly Glu Glu Val Ala Phe
        515                 520                 525

Trp Asn Asp Leu Leu Ser Lys Glu Ala Ala Lys Lys Pro Pro Lys Ile
        530                 535                 540

Lys
545
```